(12) United States Patent
Hofer et al.

(10) Patent No.: US 9,114,187 B2
(45) Date of Patent: Aug. 25, 2015

(54) ANTIMICROBIAL COATING FOR IDENTIFICATION DEVICES

(75) Inventors: Gene Allen Hofer, Lake Zurich, IL (US); David Macedon, Lemont, IL (US)

(73) Assignee: ZIH Corp., Hamilton Parish (BM)

( * ) Notice: Subject to any disclaimer, the term of this patent is extended or adjusted under 35 U.S.C. 154(b) by 806 days.

(21) Appl. No.: 11/413,499

(22) Filed: Apr. 28, 2006

(65) Prior Publication Data

US 2006/0248767 A1 Nov. 9, 2006

Related U.S. Application Data

(60) Provisional application No. 60/676,077, filed on Apr. 28, 2005.

(51) Int. Cl.
*A44C 5/00* (2006.01)
*A61L 15/46* (2006.01)
*G09F 3/00* (2006.01)

(52) U.S. Cl.
CPC ............ *A61L 15/46* (2013.01); *G09F 3/005* (2013.01); *A44C 5/00* (2013.01); *A61L 2300/104* (2013.01); *A61L 2300/202* (2013.01); *A61L 2300/404* (2013.01); *A61L 2300/606* (2013.01)

(58) Field of Classification Search
CPC .......................... A61L 2300/104; G09F 3/005
USPC ....................................................... 428/411.1
See application file for complete search history.

(56) References Cited

U.S. PATENT DOCUMENTS

| | | |
|---|---|---|
| 5,364,133 A | 11/1994 | Hofer et al. |
| 5,528,222 A | 6/1996 | Moskowitz et al. |
| 5,574,470 A | 11/1996 | de Vall |
| 5,646,592 A | 7/1997 | Tuttle |
| 5,708,419 A | 1/1998 | Isaacson et al. |
| 5,902,437 A | 5/1999 | McDonough et al. |

(Continued)

FOREIGN PATENT DOCUMENTS

| | | |
|---|---|---|
| EP | 0 071 933 A | 2/1983 |
| EP | 0 595 549 B1 | 9/1997 |
| JP | 2003164307 * | 6/2003 |

OTHER PUBLICATIONS http://web.archive.org/web/20040402172732/www.zebra.com/PA/Supplies/Labels_Thermal_Transfer.htm. Information on Z-Band 4000 from Apr. 2, 2004 accessed via http://web.archive.org on Jan. 27, 2009.*

(Continued)

*Primary Examiner* — Kortney L Klinkel
(74) *Attorney, Agent, or Firm* — Alston & Bird LLP

(57) ABSTRACT

An identification device that combines an antimicrobial coating with a printable substrate. For example, the invention includes a wristband with a face stock supporting indicia which are applied on (such as through thermal transfer printing) or through (such as through direct thermal printing) an antimicrobial layer. The antimicrobial layer is preferably a coating or varnish that is applied as the outermost layer and can bind with thermal transfer printing ink or supports pass through of direct thermal printing on a chemically receptive sublayer. The antimicrobial varnish includes varnish compounds and antimicrobial compounds such as a silver zeolite ion that is configured to react to moisture with a controlled release of microbial disinfectant. Preferably, the wristband is a hospital wristband bearing on-site printed identification indicia for a patient.

25 Claims, 8 Drawing Sheets

(56) References Cited

U.S. PATENT DOCUMENTS

| | | |
|---|---|---|
| 5,973,598 A | 10/1999 | Beigel |
| 5,973,600 A | 10/1999 | Mosher, Jr. |
| 6,070,805 A | 6/2000 | Kaufman et al. |
| 6,140,146 A | 10/2000 | Brady et al. |
| 6,147,662 A | 11/2000 | Grabau et al. |
| 6,206,292 B1 | 3/2001 | Robertz et al. |
| 6,281,795 B1 | 8/2001 | Smith et al. |
| 6,414,543 B1 | 7/2002 | Beigel et al. |
| 6,451,154 B1 | 9/2002 | Grabau et al. |
| 6,610,379 B1 | 8/2003 | Adams et al. |
| 6,667,092 B1 | 12/2003 | Brollier et al. |
| 6,693,541 B2 | 2/2004 | Egbert |
| 6,700,032 B1 | 3/2004 | Gray |
| 6,702,185 B1 | 3/2004 | Zercher |
| 6,734,887 B2 | 5/2004 | Field |
| 6,762,682 B2 | 7/2004 | Okamoto et al. |
| 6,808,118 B2 | 10/2004 | Field |
| 6,809,646 B1 | 10/2004 | Lee |
| 6,820,314 B2 | 11/2004 | Ferguson et al. |
| 6,836,215 B1 | 12/2004 | Laurash et al. |
| 6,929,413 B2 | 8/2005 | Schofield |
| 6,988,665 B2 | 1/2006 | Schofield |
| 2002/0190520 A1 | 12/2002 | Garross et al. |
| 2003/0107639 A1 | 6/2003 | Field |
| 2003/0215521 A1* | 11/2003 | Laridon et al. .......... 424/604 |
| 2004/0092896 A1 | 5/2004 | Thompson |
| 2005/0230965 A1 | 10/2005 | Field |

OTHER PUBLICATIONS

Electro-Magnetic RFID: Everything You Need to Know About Inductively coupled RFID; Motorola Indala Corporation, Rev: Nov. 11, 1997; 1996, 1997, Motorola, Inc.; 19 pgs.

Tag-It-Moving Concepts to Reality, Texas Instruments Radio Frequency Identification Systems; 13 pgs.; copyright 2000.

TIRIS News, Texas Instruments International Newsletter of the TIRIS Group; Issue No. 17, 1997; 12 pgs.

SATO DCS & Labeling Worldwide; SATO Wristbands; www.satoineurope.com; 2 pgs. Accessed Apr. 1, 2005.

Zebra Technologies International, LLC; Specification Sheet Z-Band 4000 Wristbands; 2 pgs. Available before Apr. 2, 2004.

International Search Report and Written Opinion for Application No. PCT/US2006/016204; dated Jul. 18, 2007.

Office Action (Communication) for European Application No. 06 758 725.3; dated Oct. 12, 2010.

Office Action for European Application No. 06 758 725.3; dated Apr. 15, 2013.

Office Action (Summons to attend oral proceedings) for European Application No. 06 758 725.3; dated Nov. 20, 2012.

Provision of a the minutes for European Application No. 06 758 725.3; dated Apr. 15, 2013.

* cited by examiner

ANTIMICROBIAL COATING FOR IDENTIFICATION DEVICES

CROSS-REFERENCE TO RELATED APPLICATION

This application claims priority to and the benefit of the filing date of provisional application entitled "Antimicrobial Coating For Identification Devices," assigned Ser. No. 60/676,077 and filed Apr. 28, 2005, which is hereby incorporated in its entirety by reference.

FIELD OF THE INVENTION

The present invention is related to the field of antimicrobial materials, and in particular to medical devices with antimicrobial coatings capable of reducing the spread of bacteria.

DESCRIPTION OF RELATED ART

The use of antimicrobial compounds, or other therapeutically active compounds to prevent the spread of microbes such as bacteria, algae, and fungi are well known in the prior art. In particular, antimicrobial compounds are commonly used in the medical field to protect patients from the growth or proliferation of bacteria. For example, antimicrobial compounds have been added to material of hospital bed sheets, surgical drapes, hospital gowns, medical mask, bandages, gauze, or any place a textile or textile fiber could be used to control the growth of microbes.

One example of incorporating antimicrobial compounds within medical equipment is disclosed in U.S. Pat. No. 6,700,032 which describes a bandage or wound dressing incorporating the use of an antimicrobial compound to promote better wound management and wound healing.

Additionally, U.S. Patent Application No. 2004/0092896 describes an antimicrobial sheet for environmental and human protection. These sheets are formed into rings about three inches in diameter, three quarter of an inch wide and one eight of an inch thick and are adapted to be worn on a person's wrist.

Notwithstanding the common use of antimicrobial compounds in a multitude of medical devices, the antimicrobial compounds sometimes change desirable properties of the medical devices. Therefore, there is still a need for improvements in the use of antimicrobial components with medical devices.

Therefore, it would be advantageous to have medical devices that retain their original function while simultaneously providing antimicrobial protection. It would also be advantageous if the components of the devices were economical to manufacture.

BRIEF SUMMARY OF THE INVENTION

The present invention addresses the above needs, and achieves other advantages, by providing an identification device that combines an antimicrobial coating with a printable substrate. For example, the invention includes a wristband with a face stock supporting indicia which are applied on (such as through thermal transfer printing) or through (such as through direct thermal printing) an antimicrobial layer. The antimicrobial layer is preferably a coating or varnish that is applied as the outermost layer and can bind with thermal transfer printing ink or supports pass through of direct thermal printing onto a chemically receptive sublayer. The antimicrobial varnish includes varnish compounds and antimicrobial compounds such as a silver zeolite ion that is configured to react to moisture to produce a controlled release of microbial disinfectant. Preferably, the wristband is a hospital wristband bearing on-site printed identification indicia for a patient.

In one embodiment, the present invention includes a medical device with an antimicrobial coating that bears printed indicia. The printed indicia is either printed directly onto a printable overvarnish that includes antimicrobial compounds, or is transferred through a UV curable overvarnish containing antimicrobial compounds and printed onto an imaging chemical layer.

In one aspect, the medical device is a wristband and the indicia are identifying indicia for a patient. Included in the wristband is a face stock, a protective layer over the face stock, an antimicrobial coating over the protective layer, and identifying indicia supported or permitted thereby.

In another aspect, the wristband is generally rectangular and includes a pair of opposing long edges and a pair of opposing short edges. The face stock includes two portions, a body portion that supports the antimicrobial coating and the indicia and a connector portion that is configured to be secured at its free end to the body portion when encircling a wrist or appendage.

Connectors may be used to connect the connector portion to the body portion, such as a clasp or clip that uses an insert for passing through communicating holes in the body and connector portions. Alternatively, a crack and peel connector may be employed that includes an adhesive patch covered by a cover. Removal of the cover reveals the adhesive patch which is pressure sensitive and adheres the opposing ends of the face stock together when the ends are applied to form the loop of the wristband.

The present invention has many advantages. For example, medical devices (such as the wristband) of the present invention with indicia and an antimicrobial coating can be used within potentially contaminated environments that require on-demand printing with variable information, such as identification information. For example, in a hospital environment, patients may be provided identification wristbands that include indicia information such as name, sex, and medical history. Thus, the patient is identified and at the same time protected by the antimicrobial coating from dangerous bacteria that could aggravate the patient's medical condition.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figures 1, 2:
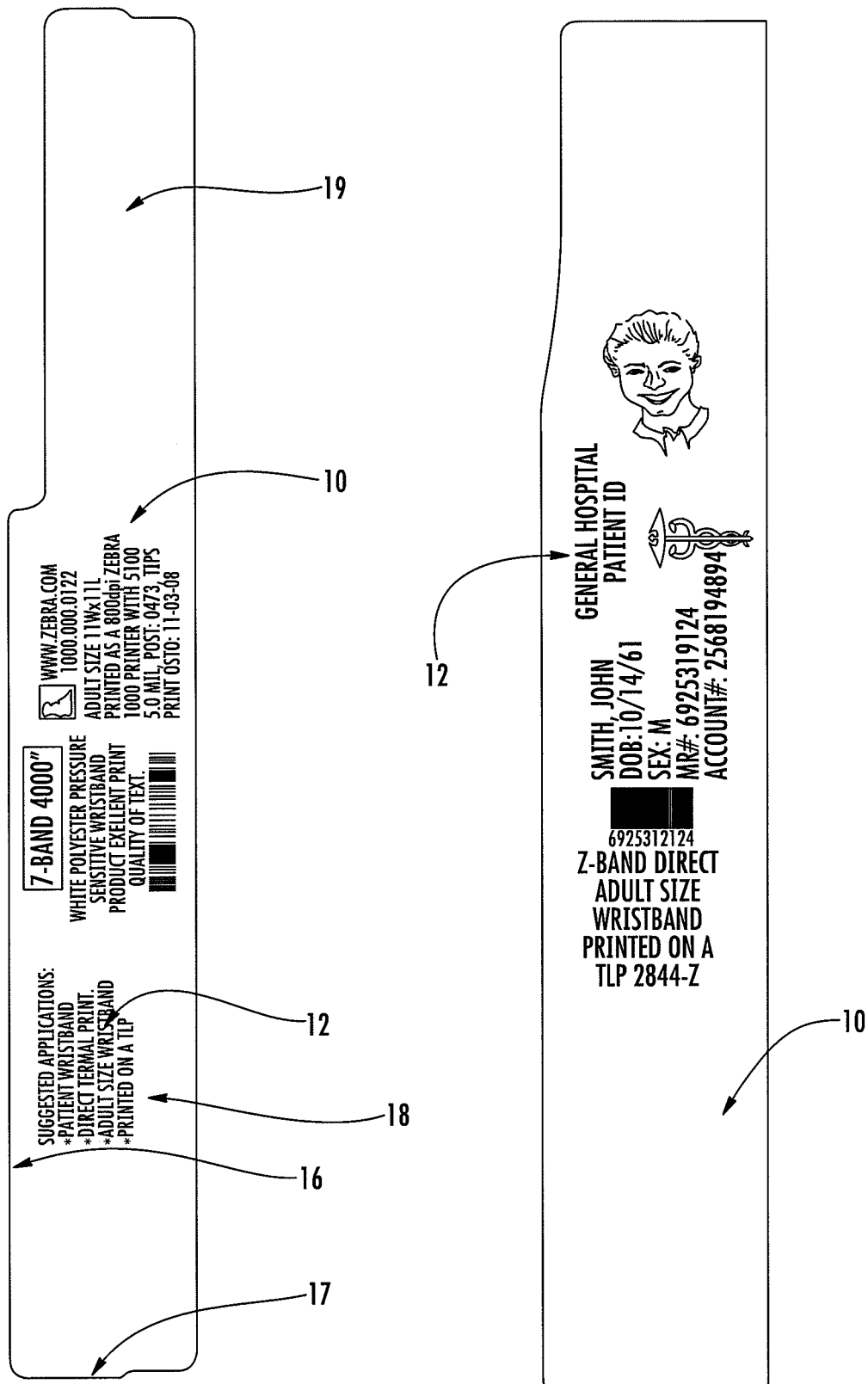
FIG. 1 is a plain view of an antimicrobial identification wristband of one embodiment of the present invention including a crack and peel fastener.
FIG. 2 is a plain view of an antimicrobial identification wristband according to another embodiment of the present invention including a crack and peel fastener.
Figure 5:
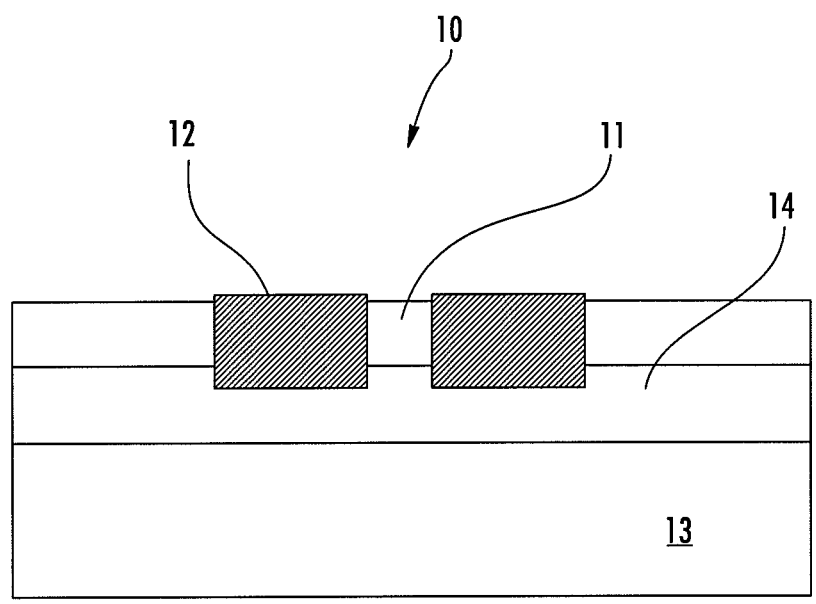
FIG. 5 is a cross-sectional diagram of the antimicrobial identification wristband of FIG. 1 showing an antimicrobial varnish layer and print indicia of the wristband.

Generally described, the present invention is directed to identification devices with an antimicrobial coating 11 supporting printing of indicia 12 thereon or through, such as a wristband 10 of one embodiment of the present invention shown in FIGS. 1 and 5. The wristband 10 includes a face stock 13, a protective top coating 14, and a layer of antimicrobial coating 11, or "overvarnish," containing antimicrobial compounds, as shown in FIG. 5. As shown in greater detail below, different embodiments of the identification devices of the present invention are designed to be compatible with various printing procedures such as direct thermal printing and thermal transfer printing.

As used herein, the term "identification device" may also apply to other devices benefiting from, or requiring, printing through or on antimicrobial layers or components. For example, within the purview of the present invention are plaques, plates and identification badges bearing the indicia 12 and the overvarnish 11, or other antimicrobial layer of protectant that allows for printing. Notably, the identification device could be a component of an overall larger device, especially a device benefiting from antimicrobial properties, such as an implant or personalized article of clothing.

The term "facestock" as used herein denotes generally the type of material used to form the supporting structure of the wristband or other identification device and is capable of retaining the print indicia 12 in combination with the protective coating 14, without the antimicrobial overvarnish 11. The term "antimicrobial" as used herein denotes a substance with the ability to control the breeding, growing and proliferation of microorganisms.

Referring again to FIGS. 1 and 5, the face stock 13 of the wristband 10 includes a pair of long edges 16, a pair of short edges 17, a body portion 18 and a connector portion 19. The body portion 18 is rectangular and is defined between about two-thirds of the two long edges 16 and one of the short edges 17. The body portion 18 is relatively wider than the connector portion 19. The connector portion 19 is similarly rectangular, but is narrow and shorter than the body portion 18, being defined between the remaining one third of the two long edges 16 and the other one of the short edges 17.

The body portion 18 being relatively wide provides a good supporting surface for the indicia 12, which in the illustrated embodiment of FIG. 1 includes three panels of print indicia and a barcode symbol. The connector portion 19 is relatively slender, allowing it to be wrapped around a wrist or appendage of a wearer first and then covered over by the body portion 18 so that the indicia 12 remain visible.

In the embodiment illustrated in FIG. 1, the wristband 10 is attached to the user through the use of an adhesive patch (not shown) supported on an underside of the body portion 18 near the short edge or on the topside of the connector portion 19 near the short edge (or both), as shown in FIG. 1. A cover (not shown) extends over the adhesive patch and can be removed using a "crack and peel" method. In this method, the user exposes the adhesive patch located on one end of the wristband and wraps the adhesive end onto the opposite end to secure the wristband in a closed loop. The cover, for example, may include a polyester release liner and the adhesive patch an acrylic adhesive that is pressure sensitive, allowing it to be compressed between the body and connector portions 18, 19 for sealing.

The face stock 13 of the embodiment illustrated in FIGS. 1 and 5 is preferably constructed from a tough synthetic material, such as from polypropylene, polyester, polyethylene or woven nylon. Alternatively, the face stock could be constructed from a natural material such as a paper material or cotton textile. Generally, it is desirable for the face stock to be relatively tough to resist breakage, flexible to allow bending into a loop and be able to withstand the heat of printing. In other embodiments, such as antimicrobial identification badges, these properties may vary, such as not requiring flexibility due to its use as a badge.

Figure 3:
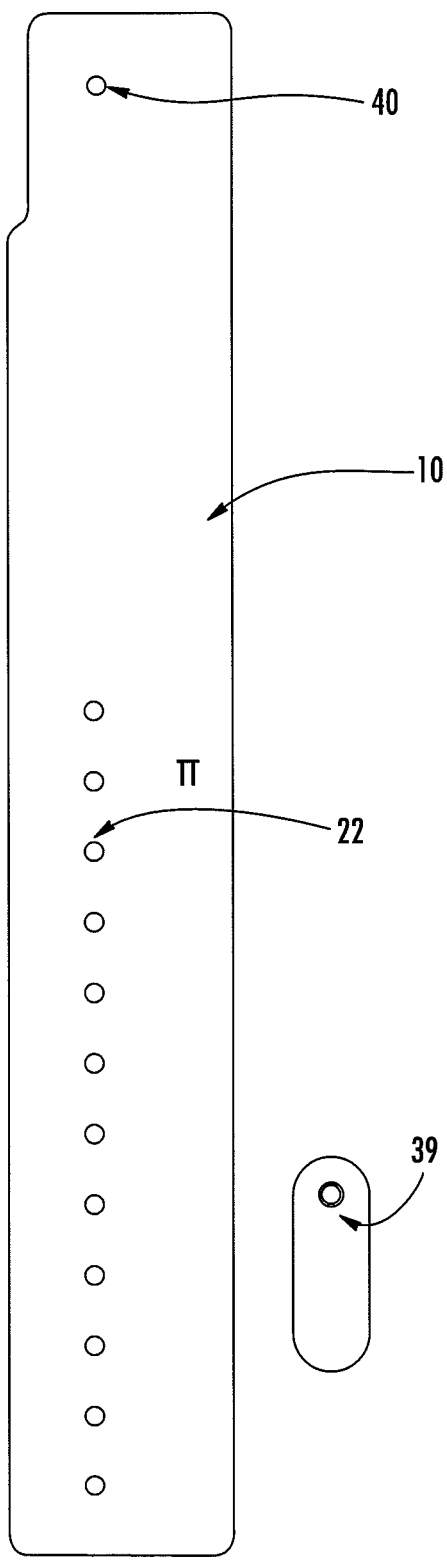
FIG. 3 is a plain view of an antimicrobial identification wristband according to yet another embodiment of the present invention including a clip fastener.
Figure 4:
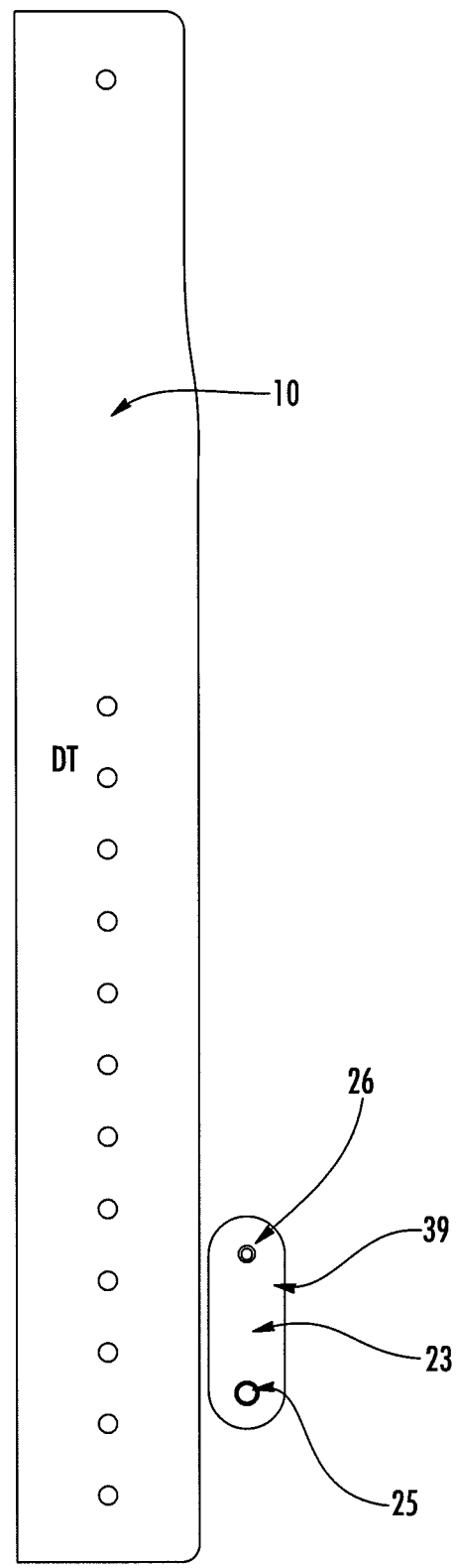
FIG. 4 is a plain view of an antimicrobial identification wristband according to still another embodiment of the present invention including a clip fastener.

The face stock 13 of the wristband 10 can have other shapes and lengths and still be within the purview of the present invention. For example, the body portion 18 may be three fourths of the length of the wrist band 10 and transition therefrom to the connector portion 19 by an inward slope along one of the long edges 16, as shown in FIG. 2. This differs from the sudden notch that marks the transition between the body portion 18 and connector portion 19 on the embodiment shown in FIG. 1. FIGS. 3 and 4 illustrate still other embodiments of the wristband 10 of the present invention with variations in the shape of the face stock 13. In other embodiments, identification devices such as the wristbands shown in FIGS. 1 and 2 can be further configured to include radio frequency identification (RFID) functionality.

Other fasteners may be used to connect the wristband 10 of the present invention into a loop. For example, in the embodiments illustrated in FIGS. 3 and 4, the wristband 10 includes a plastic clip 39 which connects to the opposing end via one of a plurality of holes 22. In particular, one of the holes 40 is positioned near the free end of the connector portion 19 and a line of the holes 22 are spaced along the body portion 18. The plastic clip 39 includes a base which is a plastic rectangular sheet with rounded ends. Across a middle portion of the base is a thinned section 24, at one end is supported an opening 25 and at the other end is supported an insert 26. The thinned section 24 allows the base to be bent over on itself for insertion of the insert 26 through an overlapping pair of the holes 22, 40 (when the portions 19, 20 are overlapped to form the loop) and into the opening 25, thereby locking the ends of the wrist band 10 together. Advantageously, the plurality of holes allows the user to adjust the diameter of the band to fit their wrist.

Dimensionally, the wristband 10 of the present invention may vary in overall length, width and thicknesses, although they typically should be sized to fit most persons. For example, the wristband may be 1 inch wide, 11 inches long and about an eighth of an inch thick and fit most normal adult persons. Wristbands intended to be used by infants or small children may be shorter than those intended to be worn by adults. Of course the dimensions and shapes of the face stock 13 can be varied for attachment to animals or other objects and not people.

The wrist band 10 illustrated in FIGS. 1 and 5 further comprises the top coating 14 which is a protective layer that is applied to the face stock 13. Preferably, the top coating 14 is evenly applied and is thermal transfer compatible, i.e., capable of receiving the thermal transfer ink to form the indicia 12, as shown in FIG. 5. In addition, the top coating 14 preferably is water resistant or hydrophobic to protect the face stock 13 from weakening and contamination. For example, the top coating may comprise a resin or a polymer that effectively seals the face stock 13 from the environment. In one embodiment, the top coating 14 comprises resin and a plurality of fillers and binders. In addition, various pigments can be added for color.

The layer of overvarnish 11 is the final outer layer that can be applied to one, or both sides, of the top coating 14 over the body portion 18 or connector portion 19 depending upon the expected exposure of the wristband 10 to microbes. Preferably, the overvarnish is a water-based varnish that is applicable in an even layer and includes some type of antimicrobial compound. In addition, the overvarnish 11 is receptive to thermal transfer ink printing as shown in FIG. 5. The smooth and uniform coating displayed by water based overvarnish makes it particularly receptive to thermal transfer ink printing. In addition, water based overvarnish holds antimicrobial particles in suspension, thereby allowing for an distribution of antimicrobial compounds within the printing area. In one embodiment, the water based overvarnish contains a combination of resins, water, and ammonia.

In one embodiment, the antimicrobial compounds contained within the water based overvarnish 11 are silver zeolites. Generally defined, a zeolite is a mineral having a porous structure. There are approximately four dozen recognized naturally occurring zeolite minerals and many more synthetic varieties. Natural zeolites often form when volcanic rocks and ash layers react with alkaline groundwater. In addition, there are several types of synthetic zeolites that form by a process of slow crystallization of a silica-alumina gel in the presence of alkalis and organic templates. Some of the more common zeolites are analcime, chabazite, heulandite, natrolite, phillissite, and stillbite. An exemplary mineral formula for natrolite is $Na_2Al_2Si_3O_{10} \cdot 2H_2O$.

Antimicrobial powders may also be used that include a soluble glass and antimicrobial silver ions. Glass generally is known as a material with high chemical inertness. However, it is possible to lower the chemical inertness by altering its structure. Glass also retains metals as ions. The presence of water or moisture will release the metal (silver) ions, which function as antimicrobial materials, gradually. One commercial example of the glass based product is Ion Pure® from Ishizuka Glass.

More specifically defined, zeolites are framework silicates consisting of interlocking tetrahedrons of $SiO_4$ and $AlO_4$. In order to be a zeolite, the ratio $(Si+Al)/O$ must equal ½. Zeolites have a negatively charged, hydrated alumino-silicate structure comprising large vacant spaces or cages that allow space for large cations such as sodium, potassium, barium, and calcium and even relatively large molecules and action groups such as water, ammonia, carbonate ions and nitrate ions. The negatively charged aluminum-silicate structure attracts and accommodates the positive cations listed above, i.e., NA, K, Ca, Mg, and others. The large vacant spaces of the zeolite structure allow for the easy movement of the resident ions and molecules into and out of the structure.

In general, zeolites are characterized by their ability to lose and absorb water without damage to their crystal structures. This characteristic makes zeolites useful in a number of commercial applications. For example, zeolites are commonly used to perform ion exchange, filtering, odor removal, chemical sieve and gas absorption tasks. One of the most well-known uses of zeolites is in water softeners. Water having significant quantities of calcium is often referred to as being "hard." Hard water is conducive to the growth of scum. The process of softening water involves passes the hard water through a plurality of zeolites charged with the much less damaging sodium ions. As the hard water passes through the zeolites, the calcium is exchanged for the sodium ions. In similar fashion, zeolites can absorb ions and molecules and this act as a filter for odor control, toxin removal, and as a chemical sieve.

Figure 10:
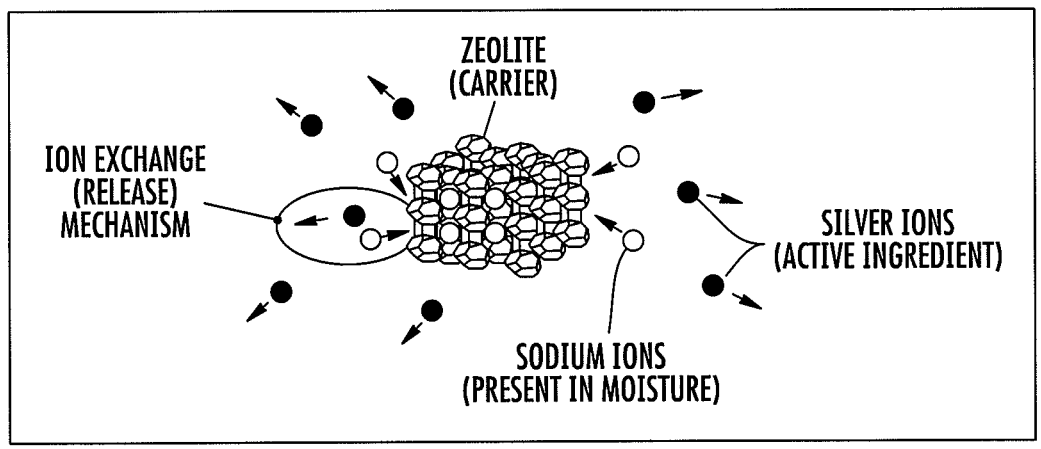
FIG. 10 is a diagram of a zeolite ion exchange process.

As mentioned above, in one embodiment of the present invention, silver zeolite represents the antimicrobial compound used in conjunction with water based overvarnish. As illustrated in FIG. 10, the zeolite structure contains a plurality of silver ions. When exposed to moisture, sodium ions (present in the moisture) are exchanged for the silver ions.

Preferable, the overvarnish 11 includes AgION™ brand silver zeolite compounds for its antimicrobial properties. As with all silver zeolite compounds, AgION™ is a compound containing silver ions (the active ingredient) bonded to a ceramic material that is completely inert (a zeolite carrier). Ambient moisture in the air causes low-level release that effectively maintains the antimicrobial properties of the overvarnish 11. As humidity increases, more silver is released. Ultimately, the powerful antimicrobial silver ions kill microbes such as bacteria, fungi, and algae. In particular, the silver ions interfere with the nutrients that sustain bacteria, thereby providing the antimicrobial effects.

It should be understood that any number of antimicrobial compounds compatible with the varnish, or other binding or coating compound used in the overvarnish 11, are within the scope of the present invention. In another example, a compound in the overvarnish 11 used to prevent the spread of bacteria may be "Inorganic Antibacterial XAW10D," produced by SINANEN-ZEOMIC Corporation. As with AgION™, antibacterial Zeomic is a mineral zeolite composite containing silver ions.

In addition, although the embodiments described above use silver zeolites as the antimicrobial compound, other embodiments use antimicrobial substances such as Triclosan. Triclosan exhibits similar properties as the silver zeolites described above, i.e., it is a highly effective antimicrobial agent that is mixable and compatible with the varnish. Triclosan is manufactured by Ciba Specialty Chemical Products under the trade names IRGASAN and IRGACARE and has a molecular formula of $C_{12}H_7CL_3O_2$.

The overvarnish 11 is created by mixing the water-based varnish with the antimicrobial compound. In one embodiment, the anti-mcirobial compund such as AgION™ comes in a powder form and is mixed with a water based varnish prior to being applied to the wristband. As discussed in greater detail below, the mixed water based varnish and antimicrobial compound is applied to the wristband using a flexographic printing press.

Figure 6:
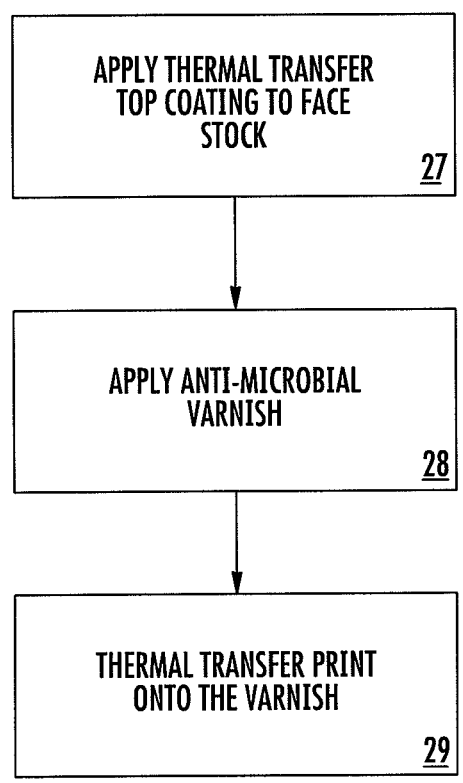
FIG. 6 is a flow diagram of a method of another embodiment of the present invention for applying identification information to an antimicrobial identification device using a thermal transfer printing process.

FIG. 6 illustrates the steps for construction of the wristband 10 using thermal transfer printing. In step 27, the thermal transfer receptive coating 14 is applied to the surfaces of the face stock 13, preferably on the body portion 18. At step 28, the coating of water based overvarnish 11 containing antimicrobial compounds (which were mixed as described above) is applied to the face stock 13. Application of the overvarnish 11 is preferably by an even and thorough application process. For example, the water based overvarnish 11 may be applied over the entire face stock 13 using a flexographic printing press. Alternatively, the flexographic printing press can be configured to apply the overvarnish only to specific areas of the face stock 13 that are expected to experience exposure to microbes or contaminants. Preferably, however, the overvarnish 11 is uniformly applied across the entire surface area of one side of the face stock 13.

Figure 7:
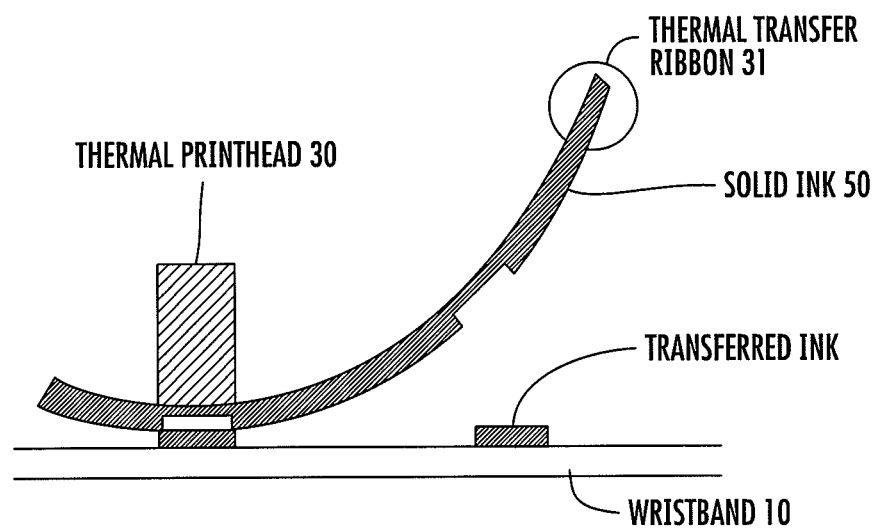
FIG. 7 is a diagram of the thermal transfer printing process.

After the water based overvarnish is applied to the wristband, identification information is printed onto the wristband at step 29 using a thermal transfer printing process, as shown in FIG. 7. In the thermal transfer printing process, a thermal transfer ribbon 31 is passed between a thermal print head 30 and the wristband 10 so that the ink 50 of the thermal transfer ribbon 31 is imprinted by the heat of the print head 30 directly onto the overvarnish 11 to form the indicia 12.

A variety of ribbon types are available and can be used in conjunction with the thermal transfer printing process and the wristband 10 of the present invention. For example, the ribbons can be wax ribbons, wax/resin ribbons, or resin ribbons. In addition, thermal ribbons come in a variety of colors or print solely with black ink.

Figure 9:
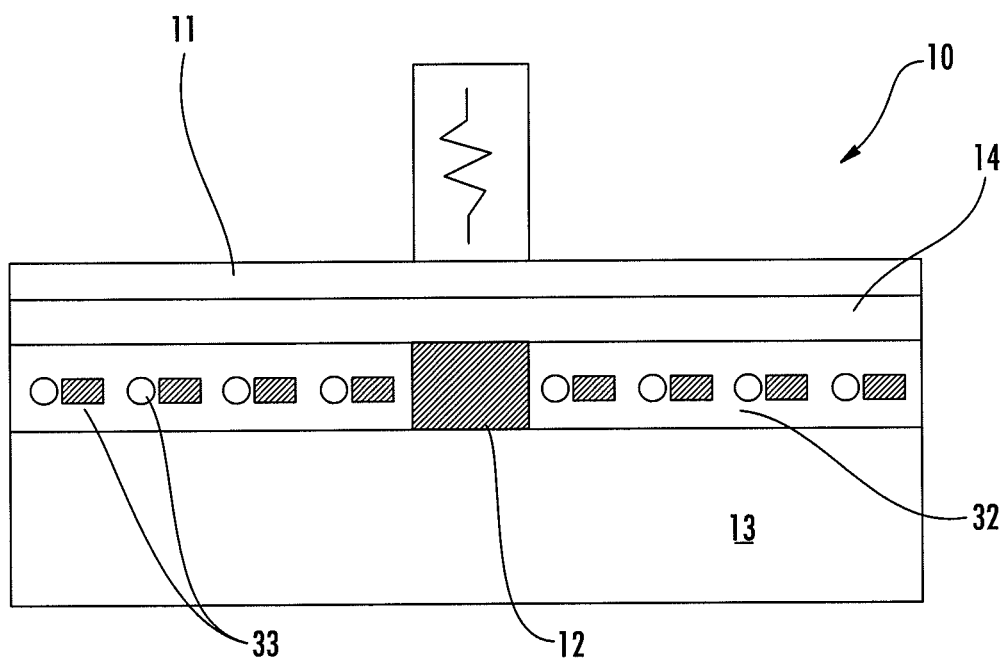
FIG. 9 is a diagram of the direct thermal printing process of FIG. 8.

In another embodiment of the present invention, the wristband 10 of the present invention is configured for printing on with a direct thermal printing process. As shown in FIG. 9, the wristband 10 in this embodiment includes an additional layer having thermal imaging chemicals 32, such as one or more color formers 33 in a direct thermal paper. The thermal imaging chemical layer 32 is positioned underneath the protective top coating 14 and extends over the face stock 13 of the wristband 10. The top coating 14 protects the thin layer of thermal imaging chemicals 32 from the environment, thereby limiting its exposure to water, blood, alcohol, alcohol from soaps, or soaps that could inadvertently alter the chemistry's appearance. The direct thermal imaging chemicals 32 are generally any form of heat sensitive material that will manifest portions of the indicia 12 with the application of heat.

The wristband 10 also preferably includes a UV curable overvarnish mixed with an antimicrobial agent to form the overvarnish 11 layer. The UV curable nature of the overvarnish allows it to be used with the high heat of direct thermal printing and still preserves its antimicrobial properties. Much like the protective top coating 14, the UV curable overvarnish protects the chemistry layer 32 from exposure to substances typically found in hospital, such as water, blood, and alcohol. Without protection from the UV curable overvarnish, the chemistry layer 32 can be activated, turning the chemistry layer 32 black or otherwise discolored. The result being the degradation of all or portions of the indicia 12 (e.g. bar codes and/or human readable information) which might lead to errors and reduce patient safety.

Figure 8:
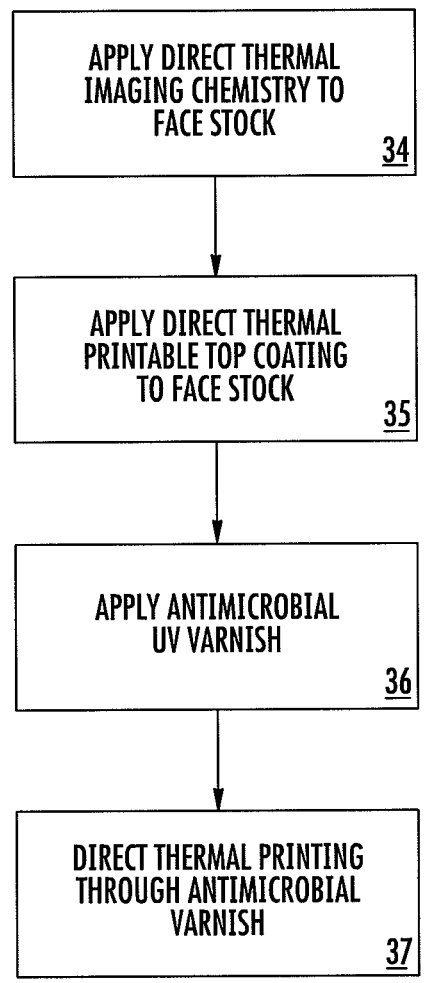
FIG. 8 is a flow diagram of a method of another embodiment of the present invention for applying identification information to an antimicrobial identification device using a direct thermal printing process.

FIG. 8 illustrates the steps for constructing the wristband 10 shown in FIG. 9. At step 34, the thermal imaging chemical layer 32 or chemistry is applied in a layer to the face stock 13. At step 35, the protective top coating 14 is applied, as described in step 27 above. Then, in step 36, a coating of UV curable overvarnish containing antimicrobial compounds is applied to the face stock 13. For example, the UV curable overvarnish is applied using a process known as flexographic printing.

The flexographic printing process may incorporate a form of rotary web letterpress that uses one or more relief plates comprised of flexible rubber or photopolymer plates. This allows the application of water-based or UV curable inks or varnishes to a material such as the protective coating 14 on the face stock 13 and chemical layer 32. In this embodiment, the flexographic printing press applies the coating of UV curable overvarnish 11 containing antimicrobial sliver zeolite.

In step 37, the indicia 12 are printed onto the wristband 10 using a direct thermal printing method. Under the direct thermal printing method, a heated printhead 38 transfers an image directly onto the heat sensitive imaging chemical layer 32 located within the wristband 10. In particular, the image is formed when the heat from the printhead causes the heat sensitive material to darken or burn and form the indicia 12, as shown in FIG. 9.

The present invention has many advantages. For example, medical devices (such as the wristband 10) of the present invention with indicia 12 and an antimicrobial coating 11 can be used within potentially contaminated environments that require on-demand printing with variable information, such as identification information. For example, in a hospital environment, patients may be provided identification wristbands 10 that include indicia 12 information such as name, sex, and medical history. Thus, the patient is identified and at the same time protected by the antimicrobial coating 11 from dangerous bacteria that could aggravate the patient's medical condition.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An identification device comprising:
   a face stock;
   a protective coating positioned at least one of proximate or adjacent to at least a portion of at least one surface of said face stock, wherein the protective layer consists of resin and a plurality of fillers and binders; and
   a water-based antimicrobial varnish layer receptive to a thermal transfer ink printing process and positioned on at least a portion of said protective coating, said antimicrobial layer comprising a silver zeolite containing silver ions such that upon exposure of the device to moisture at least a portion of the silver ions are released to maintain an antimicrobial property of the antimicrobial layer.

2. The identification device according to claim 1, wherein said antimicrobial coating comprises a Triclosan compound.

3. The identification device according to claim 1, wherein said protective coating is hydrophobic.

4. The identification device according to claim 1, wherein said face stock comprises a flexible material.

5. The identification device according to claim 1, wherein said face stock comprises at least one of a polypropylene, polyester, polyethylene, and woven nylon material.

6. The identification device according to claim 1, further comprising a radio frequency identification device.

7. The identification device according to claim 1, wherein the identification device is a wristband.

8. The identification device according to claim 7, wherein the wristband comprises a pair of long edges, a pair of short edges, a body portion and a connector portion, and wherein said connector portion is shorter and narrower than said body portion.

9. The identification device according to claim 8, wherein said connector portion is an adhesive patch.

10. The identification device according to claim 8, wherein said antimicrobial varnish layer and said indicia are located on at least a portion of the body portion.

11. The identification device according to claim 1 further comprising indicia imprinted on said antimicrobial varnish layer using the thermal transfer printing process.

12. The identification device according to claim 11, wherein said indicia comprises identifying indicia for a patient.

13. The identification device according to claim 12, wherein said antimicrobial coating comprises a Triclosan compound.

14. An identification device comprising:
   a face stock;
   a thermal chemical imaging layer applied to at least a portion of at least one surface of said face stock;
   an ultraviolet curable antimicrobial layer positioned proximate to at least a portion of said thermal chemical imaging layer and configured to enable direct thermal printing onto the thermal chemical imaging layer through the antimicrobial layer; and
   a protective layer positioned between, and adjacent to, said thermal chemical imaging layer and said antimicrobial layer, wherein the protective layer consists of resin and a plurality of fillers and binders.

15. The identification device according to claim 14, wherein said thermal chemical imaging layer comprises at least one heat sensitive thermal imaging chemical capable of manifesting indicia upon the application of heat thereto.

16. The identification device according to claim 14, wherein said antimicrobial layer comprises a silver zeolite compound.

17. The identification device according to claim 14, further comprising a radio frequency identification device.

18. The identification device according to claim 14, wherein the identification device is a wristband.

19. The identification device according to claim 14 further comprising indicia imprinted on said chemical layer using the direct thermal printing.

20. A method of constructing an identification device comprising:
   providing a face stock;
   positioning a protective coating at least one of proximate or adjacent to at least a portion of at least one surface of the face stock, wherein the protective layer consists of resin and a plurality of fillers and binders; and
   applying a water-based antimicrobial varnish layer receptive to a thermal transfer printing process on at least a portion of the protective coating, said antimicrobial layer comprising a silver zeolite containing silver ions such that upon exposure of the device to moisture at least a portion of the silver ions are released to maintain an antimicrobial property of the antimicrobial layer.

21. The method of claim 20, wherein positioning comprises applying the protective coating directly onto the face stock.

22. The method of claim 20, wherein applying comprises applying the antimicrobial coating using a flexographic printing press.

23. The method of claim 20 further comprising imprinting indicia on at least a portion of the antimicrobial varnish layer using the thermal transfer printing process.

24. A method of constructing an identification device comprising:
   providing a face stock;
   applying a thermal chemical imaging layer on at least one surface of at least a portion of the face stock; and
   positioning an ultraviolet curable antimicrobial layer proximate to at least a portion of the thermal chemical imaging layer, wherein the ultraviolet curable antimicrobial layer is configured to enable direct thermal printing onto the thermal chemical imaging layer through the antimicrobial layer; and
   positioning a protective layer between, and adjacent to, said thermal chemical imaging layer and said antimicrobial layer, wherein the protective layer consists of resin and a plurality of fillers and binders.

25. The method of claim 24 further comprising printing indicia on at least a portion of the thermal chemical imaging layer using the direct thermal printing process.

* * * * *